(12) United States Patent
Meetz et al.

(10) Patent No.: US 8,965,080 B2
(45) Date of Patent: Feb. 24, 2015

(54) PERFUSION IMAGING

(75) Inventors: Kirsten R. Meetz, Hamburg (DE);
Ingwer-Curt Carlsen, Hamburg (DE);
Jorg Bredno, San Francisco, CA (US)

(73) Assignee: Koninklijke Philips N.V., Eindhoven (NL)

( * ) Notice: Subject to any disclaimer, the term of this patent is extended or adjusted under 35 U.S.C. 154(b) by 440 days.

(21) Appl. No.: 13/256,497

(22) PCT Filed: Feb. 18, 2010

(86) PCT No.: PCT/IB2010/050730
§ 371 (c)(1),
(2), (4) Date: Sep. 14, 2011

(87) PCT Pub. No.: WO2010/109356
PCT Pub. Date: Sep. 30, 2010

(65) Prior Publication Data
US 2012/0008846 A1    Jan. 12, 2012

Related U.S. Application Data

(60) Provisional application No. 61/163,572, filed on Mar. 26, 2009.

(51) Int. Cl.
*G06K 9/00* (2006.01)
*G06F 19/00* (2011.01)
*A61B 6/03* (2006.01)
*A61B 6/00* (2006.01)
*A61B 5/026* (2006.01)

(52) U.S. Cl.
CPC ............ *G06F 19/345* (2013.01); *A61B 5/0263* (2013.01); *A61B 6/032* (2013.01); *A61B 6/481* (2013.01); *A61B 6/501* (2013.01); *A61B 6/504* (2013.01); *A61B 6/507* (2013.01); *G06F 19/321* (2013.01); *G06F 19/325* (2013.01)
USPC .......................................................... 382/128

(58) Field of Classification Search
None
See application file for complete search history.

(56) References Cited

U.S. PATENT DOCUMENTS

| 5,986,662 | A  | * | 11/1999 | Argiro et al. | ............... | 345/424 |
| 6,584,216 | B1 | * | 6/2003  | Nyul et al.   | ............... | 382/131 |
| 6,787,109 | B2 |   | 9/2004  | Haar et al.   |   |   |
| 7,400,756 | B2 |   | 7/2008  | Klotz         |   |   |
| 7,536,041 | B2 |   | 5/2009  | Pekar et al.  |   |   |

(Continued)

FOREIGN PATENT DOCUMENTS

| JP | 2001223946 A | 8/2001  |
|----|--------------|---------|
| JP | 2004357866 A | 12/2004 |

(Continued)

OTHER PUBLICATIONS

Tomandl, B. F., et al.; Comprehensive Imaging of Ischemic Stroke with Multisection CT; 2003; Radiographics, The Radiological Society of North America; 23(3)565-592.

*Primary Examiner* — Shervin Nakhjavan

(57) ABSTRACT

A method includes executing, via a data analyzer (122), computer executable instructions that select, without user interaction, a processing protocol (212) from an electronic repository (210) of protocols based on imaging data and non-imaging data corresponding to the patient, processing, via the data analyzer (122), functional imaging data for a subject with the selected processing protocol (212) under a first processing mode, and performing a plausibility check on the processed data.

24 Claims, 3 Drawing Sheets

(56) References Cited

U.S. PATENT DOCUMENTS

| | | | |
|---|---|---|---|
| 7,580,737 B2 | 8/2009 | Wintermark et al. | |
| 7,986,821 B2 * | 7/2011 | DuGal | 382/128 |
| 8,036,434 B2 | 10/2011 | Hewett et al. | |
| 2003/0083565 A1 * | 5/2003 | Toth et al. | 600/407 |
| 2003/0139944 A1 * | 7/2003 | Carlsen et al. | 705/2 |
| 2004/0044282 A1 * | 3/2004 | Mixon et al. | 600/427 |
| 2004/0093166 A1 * | 5/2004 | Kil | 702/19 |
| 2005/0267348 A1 * | 12/2005 | Wollenweber et al. | 600/407 |
| 2006/0056691 A1 * | 3/2006 | Vaz et al. | 382/173 |
| 2007/0109294 A1 * | 5/2007 | Gotman et al. | 345/418 |
| 2007/0223801 A1 * | 9/2007 | Gundel | 382/131 |
| 2007/0239012 A1 * | 10/2007 | Boeing et al. | 600/439 |
| 2008/0044069 A1 * | 2/2008 | DuGal | 382/128 |
| 2008/0051660 A1 * | 2/2008 | Kakadaris et al. | 600/454 |
| 2008/0243759 A1 * | 10/2008 | Martin et al. | 707/1 |
| 2008/0262344 A1 * | 10/2008 | Brummett | 600/426 |
| 2008/0292049 A1 * | 11/2008 | Camus et al. | 378/21 |
| 2008/0310583 A1 * | 12/2008 | Truyen et al. | 378/8 |
| 2009/0006131 A1 | 1/2009 | Unger et al. | |
| 2009/0034812 A1 * | 2/2009 | Nowinski et al. | 382/131 |
| 2009/0190840 A1 * | 7/2009 | Gundel | 382/224 |
| 2010/0125173 A1 * | 5/2010 | Bottai | 600/300 |

FOREIGN PATENT DOCUMENTS

| | | |
|---|---|---|
| JP | 2006149446 A | 6/2006 |
| JP | 2007222325 A | 9/2007 |
| WO | 2006056798 A1 | 6/2006 |
| WO | 2006067719 A2 | 6/2006 |
| WO | 2008034182 A1 | 3/2008 |

* cited by examiner

PERFUSION IMAGING

CROSS REFERENCE TO RELATED APPLICATIONS

This application claims the benefit of U.S. provisional application Ser. No. 61/163,572 filed Mar. 26, 2009, which is incorporated herein by reference.

DESCRIPTION

The following generally relates to perfusion imaging, and finds particular application to computed tomography perfusion (CTP). However, it is also amenable to other medical imaging applications and to non-medical imaging applications, including applications where final imaging results are available after applying one or more processing steps that can be fully or partially automated and/or based on interactive user input.

Computed tomography perfusion (CTP) imaging provides information that can be used to facilitate diagnosing patients with mal-perfusion of the brain like stroke patients. In general, a typical CTP procedure includes intravenously administering a contrast agent to a patient. The patient's organ of interest, e.g. the brain is then scanned. The contrast agent causes the x-ray density in this organ to temporarily increase as the contrast agent flows through and washes out of the vascular structure of this organ.

Data is captured and images are generated for different time intervals to trace the contrast agent as it flows through the vascular structure of the brain. The resulting data can be used to identify ischemic tissue and/or differentiate between irreversibly damaged tissue (necrotic tissue, or the core of the infarct) and potentially reversibly damaged tissue (at-risk tissue, or the penumbra of the infarct), for example, in stroke patients.

Software application perfusion packages provide interactive control of the analysis of CTP image data by the user. Such packages can be used to generate visual or graphical perfusion parameter maps showing cerebral blood flow (CBF), cerebral blood volume (CBV), mean transit time (MTT) and time to peak (TTP) maps, and summary maps, based on the perfusion parameter maps, which show areas of hypo-perfusion in the brain.

Such maps help identify the core and the penumbra of an infarct and may impact the therapeutic decision making, for example, where the percentage of the core to the total ischemic area (core plus penumbra) is used to decide whether thrombolytic or other therapy should be applied in an attempt to save the potentially reversibly damaged tissue (the penumbra).

Unfortunately, such user control requires a considerable amount of user interaction, which can make the generation of the perfusion maps a time-consuming, error-prone task and/or tedious. For example, the user may have to work through a series of individual tasks such as registering image data, filtering the image data, generating perfusion maps, identifying vessels in the image data, etc. Although automating one or more of these tasks may reduce the amount of user interaction, automation is also prone to error, which may lead to incorrect diagnosis and/or therapeutic decisions.

Aspects of the present application address the above-referenced matters and others.

According to one aspect, a method includes executing, via a data analyzer, computer executable instructions that select, without user interaction, a processing protocol from an electronic repository of protocols based on imaging data and non-imaging data corresponding to the patient, processing, via the data analyzer, functional imaging data for a subject with the selected processing protocol under a first processing mode, and performing a plausibility check on the processed data.

According to another aspect, a data analyzer includes a protocol selector that selects a processing protocol from a plurality of processing protocols stored in a protocol repository based on imaging data and non-imaging data for a patient, a processor that employs the selected processing protocol to process patient data for the patient without user interaction, and a protocol modifier that modifies the selected processing protocol based on user input if the processed data fails to satisfy a plausibility check, wherein the processor employs the modified processing protocol to process patient data.

According to another aspect, a computer readable storage medium containing instructions which, when executed by a computer, cause the computer to perform the steps of: loading patient data, wherein the patient data includes input for post-processing to obtain diagnostic image data, selecting a processing protocol from a database without user interaction and based on imaging and non-imaging data for the patient, processing the patient data with the selected processing protocol without user interaction, and if the processed data fails to satisfy a plausibility check, modifying the selected processing protocol and processing the patient data with the modified processing protocol.

The invention may take form in various components and arrangements of components, and in various steps and arrangements of steps. The drawings are only for purposes of illustrating the preferred embodiments and are not to be construed as limiting the invention.

The following generally relates to processing patient data, such as image data and/or other data, using a processing protocol that is selected based on imaging data, non-imaging data, and/or other information. The processing protocol can be a previously validated protocol or a modified previously validated protocol that is modified, for example, based on the image data, non-image data, a plausibility check, and/or other information.

In one instance, processing with the selected protocol is automated in that the data is processed using the selected protocol without user interaction. In such an instance, one or more plausibility checks (automated and/or manual) can be performed during and/or after processing, and the checks can be used to facilitate determining if the protocol should be adjusted, suitable protocol adjustments and/or whether one or more of the processing steps should be performed with user interaction. The data can then be processed again using the adjusted protocol and/or in semi-automated or manual mode. In another embodiment, processing with the selected protocol is initially semi-automated or manual in that the data is processed using the protocol with user interaction for some or all of the processing steps. The above allows for tuning the processing of a study for the patient.

It is also to be appreciated that such processing may be automatically or manually switch between interactive, semi-automatic and automatic processing before, during and/or after processing of the patient data. For example, assuming that processing is initially set for fully automated processing, the system and/or a user can evaluate information such as a shape of a time concentration curve, a physiologic parameter of the patient, patient motion, information about contrast agent administration, the location of a reference vessel, a generated perfusion map, parameters such as mean transit time (MTT), cerebral blood volume (CBV), cerebral blood flow (CBF) and time to peak (TTP), the selected protocol, the available protocols, CTP image data, registration of image data, segmentation of image data, etc. and may switch the processing mode to a semi-automated mode or interactive mode. Likewise, the mode can be switched from any starting mode to one or more other modes based on available information.

Figure 1:
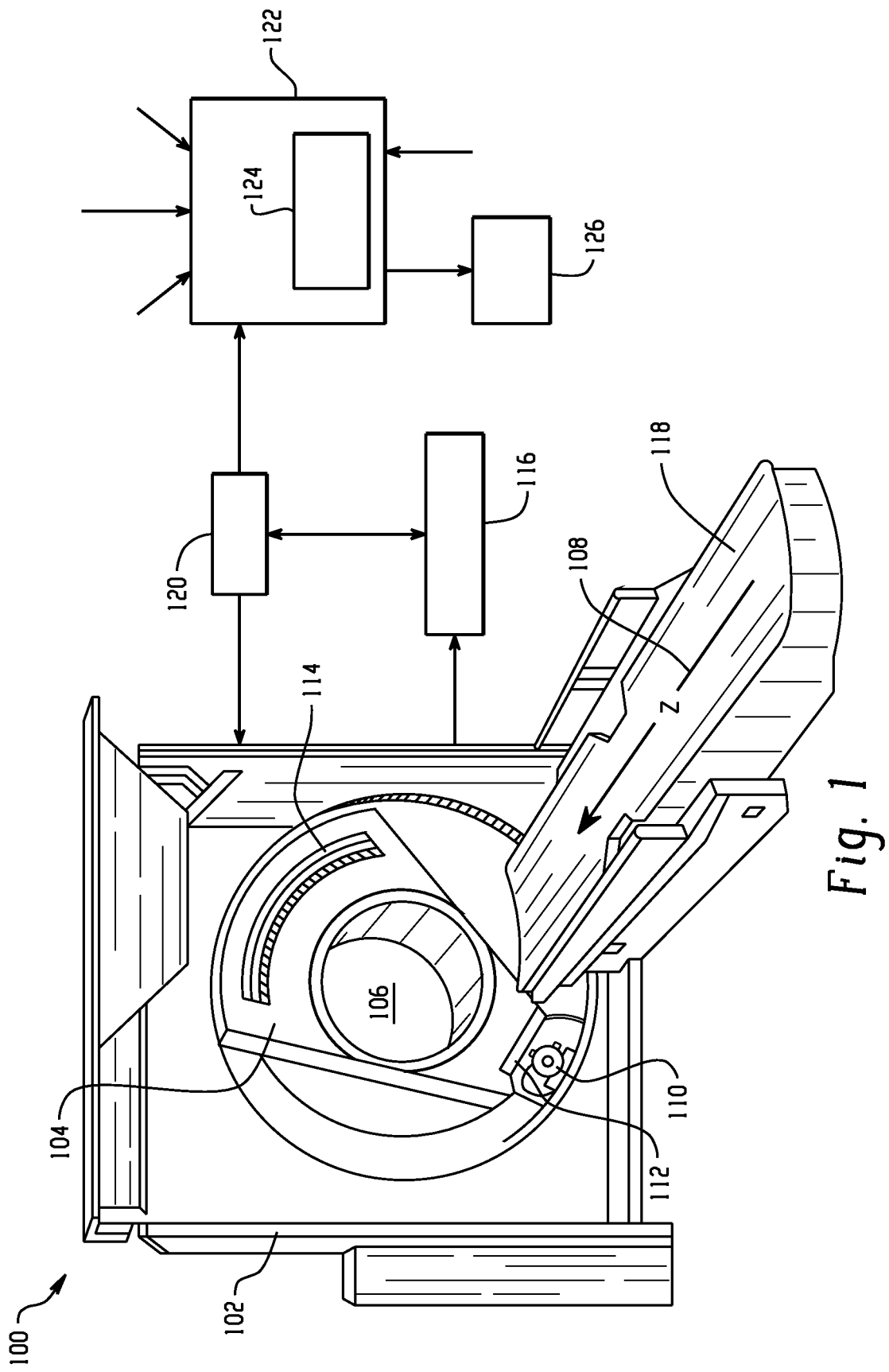
FIG. 1 illustrates a data analyzer in connection with an imaging system.

For explanatory purposes, the above is described in greater detail below in connection with processing CTP image data. Other data and/or other functional imaging data from other modalities such as MR, US, SPECT, PET, etc. can also be processed. FIG. 1 illustrates a computed tomography (CT) scanner 100 that includes a stationary gantry 102 and a rotating gantry 104, which is rotatably supported by the stationary gantry 102.

The rotating gantry 104 rotates around an examination region 106 about a longitudinal or z-axis 108. A radiation source 110, such as an x-ray tube, is supported by and rotates with the rotating gantry 104 around the examination region 106. The radiation source 110 emits radiation, which is collimated by a collimator 112 to produce a generally fan, wedge, or cone shaped radiation beam that traverses the examination region 106. A radiation sensitive detector array 114 detects photons that traverse the examination region 106 and generates projection data indicative thereof.

A reconstructor 116 reconstructs the projection data and generates volumetric image data indicative of the examination region 106, including a portion of a subject residing therein. A patient support 118, such as a couch, supports the patient for the scan. A general purpose computing system 120 serves as an operator console. Software resident on the console 120 allows the operator to control the operation of the system 100.

The scanner 100 can be used to perform a time series contrast enhanced imaging procedure such as a CTP procedure of the brain or other vascular tissue and/or other procedure. Such a procedure may include administering a contrast medium bolus, such as an intravenous iodinated contrast agent, to a subject, and then scanning the subject's brain over time. Following the administration of the contrast, the x-ray density of the brain temporarily changes as the contrast medium flows through the vascular structure of the brain. In one instance, images from the beginning of contrast uptake to its wash out after a pass through the brain are acquired.

The flow of the contrast material can be traced as it passes through the vascular structure of the brain via multiple scans. The resulting CTP image data can be used to identify ischemic tissue and/or differentiate between irreversibly damaged tissue and potentially reversibly damaged tissue, for example, in stroke patients or patients with another neurovascular disease. The scanner 100 can additionally or alternatively be used to perform other imaging procedures.

A data analyzer 122 analyzes the imaging data. In one instance, this includes generating one or more perfusion maps indicative of parameters such as a mean transit time (MTT), cerebral blood volume (CBV), cerebral blood flow (CBF), time to peak (TTP), and/or one or more other parameters, and/or a summary map based on one or more of the perfusion maps.

A protocol identifier 124 identifies a protocol for processing the CTP data. As described in greater detail below, the protocol can be identified based on various input such as non-imaging data (e.g., patient state, history, pathology, etc.), imaging data (e.g., protocol, parameters, etc.), user input and/or other input, and can be an existing protocol, a newly derived protocol, a modified protocol, and/or other protocol.

An output device 126 can be used to present data such as the CTP data, intermediate data (e.g., pre-processed data such as registered data, segmented data, filtered data, etc.), the one or more of the perfusion maps, the summary map and/or other information. Such data can be used to perform a plausibility check of the analysis. The plausibility check may include evaluating a shape of a time concentration curve (TCC), a location of a reference vessel, one or more perfusion maps, the summary map, and/or other information.

In one instance, if a clinician and/or executing computer readable instructions observes an inconsistency in a plausibility check at any step during the processing and/or believes that it is likely that the plausibility check will fail based on the selected protocol, contrast agent administration, the patient state, the clinician's experience, and/or other information, the one or more protocol parameters can be adjusted, and the data analyzer 122 can process the data with the adjusted protocol.

Alternatively or additionally, the data analyzer 122 can be run in an interactive or semi-interactive mode in which the clinician interacts with (e.g., provides input to) the data analyzer 122 while the data analyzer 122 is performing for one or more processing steps. As such, the data analyzer 122 can reduce user interaction and improve processing speed, while mitigating processing data with protocols and/or relying perfusion and/or summary maps that may lead to erroneous diagnoses and/or therapeutic decisions.

In another instance, the analysis is fully automated using a fixed, non-adjustable protocol such as described in WO 2008/034182. Unfortunately, this approach is prone to error as the protocol does not take into account patient specific parameters, plausibility checks, procedure specific information, etc., and the analysis generally does not allow for user interaction, which may be required at times to mitigate processing that may lead to erroneous diagnoses and/or therapeutic decisions.

Figure 2:
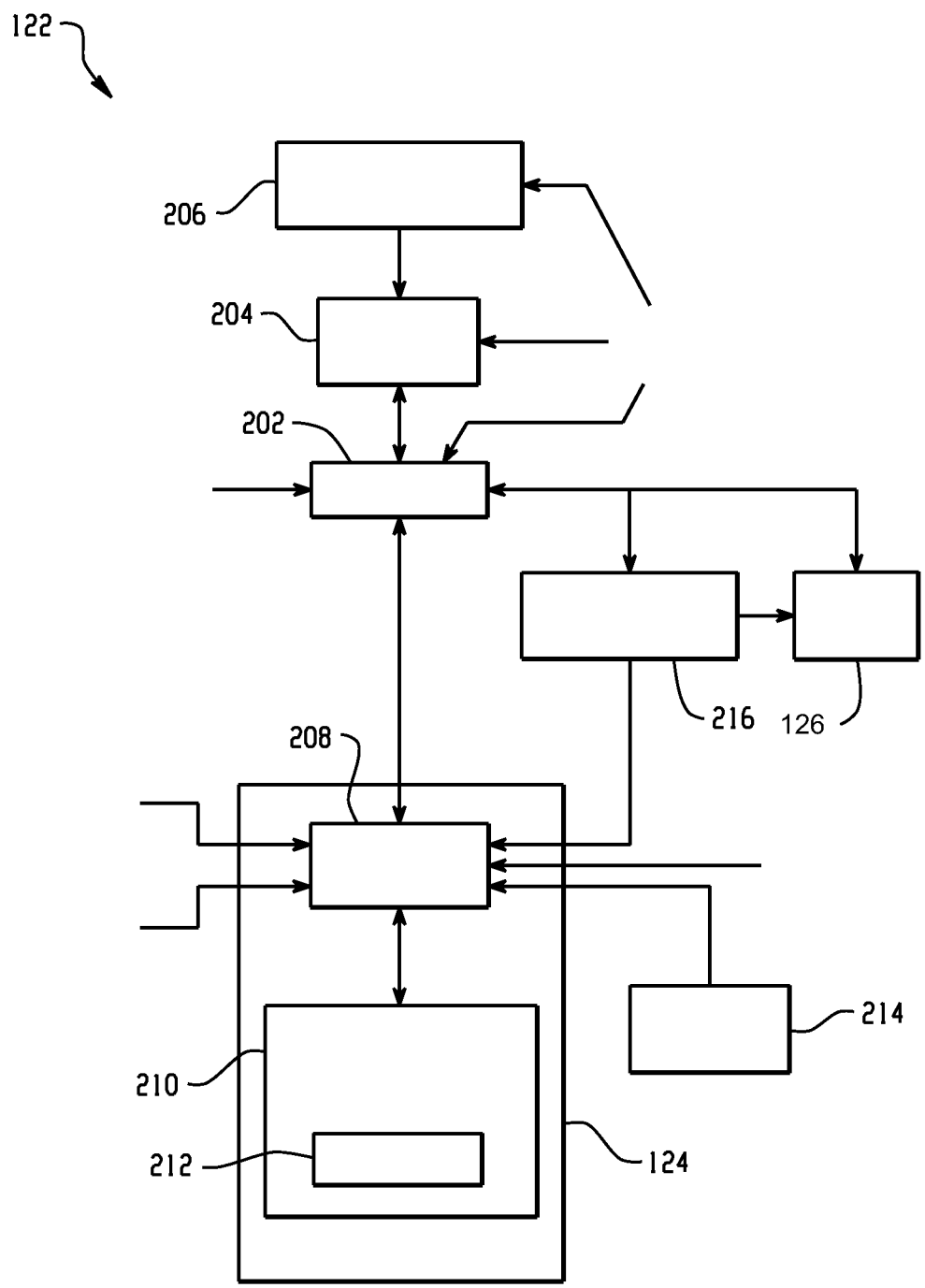
FIG. 2 illustrates an example data analyzer.

FIG. 2 illustrates a non-limiting example data analyzer 122. The data analyzer 122 includes a processor 202 that processes CTP and/or other data. In the context of CTP data analysis, the processing may include registering image data, segmenting image data, filtering image data, generating one or more perfusion masks, defining one or more vessels (e.g., reference artery, etc.) and/or the midline in the image data, generating one or more perfusion maps based on the image data and the vessels defined therein, generating a summary map based on the perfusion maps, etc.

In the illustrated example, the CTP data is generated by the scanner 100. In other embodiments, the data can be generated by a different modality or device. The data may be provided by the data generating device, or obtained from an image repository such as a data base or an archival system like a hospital information system (HIS), a radiology information system (RIS), a picture archiving and communication systems (PACS), an electronic patient record (EPR) system, and/or other system.

A mode selector 204 identifies a mode of operation for the processor 202. Suitable modes includes a fully automated mode in which the processor 202 processes the CTP data without user interaction, a partially automated or interactive mode in which one or more of the processing acts are performed with some degree of user interaction, and a manual mode in which the user manually steps through the acts. As shown, a user may interact with the processor 202 and/or the mode selector 204 to set and/or change the mode.

A user may set a default or user defined mode in a settings configuration 206, which is readable by the mode selector 204. The mode can be changed for and/or during processing. The user or mode selector 204 may select a mode for a study based on the imaging data, the non-imaging data, and/or other information. Such information may indicate that employing one of the available protocols is likely to result in not satisfying, or failing, a plausibility check, and/or that information that may affect the outcome is not considered in the selected protocol.

A protocol selector 208 identifies a processing protocol. In one instance, the identified protocol is a protocol from a protocol repository 210, which includes a plurality of protocols 212. The protocols 212 in the protocol repository 210 may be previously defined and validated protocols, and are associated with patient and/or imaging procedure characteristics. As such, patient state and/or imaging procedure parameters can be used to identify protocol candidates.

The protocol repository 210 may include protocols obtained from a patient information data base or an archival system like a HIS, a RIS, a PACS, an EPR system, and/or other system. A protocol modifier 214 and/or the user can modify a selected protocol and/or a protocol in the protocol repository 210, derive a protocol based on a protocol in the protocol repository 210, and/or select an alternative protocol from the protocol repository 210.

The protocol selector 208 can identify a protocol based on information such as the imaging data, the non-imaging data, a plausibility check, and/or user input. Examples of non-imaging data include, but are not limited to, a state of the patient (e.g., cardiovascular disease), a physiological parameter (e.g., heart rate), a neurological symptom, a neurological deficit, a known abnormality such as a vessel abnormality like a stenosis, and/or other information. Examples of imaging data include, but are not limited to, image acquisition parameters, scan timing information, contrast administration timing information, and/or other information.

The output device 126 presents the CTP data, the registered image data, the filtered imaged data, the masked image data, segmented image data, one or more identified vessels, one or more of the generated perfusion maps (MTT, CBF, CBV, etc.), time concentration curves, a summary map, and/or other information in a human readable format. As noted above, based on this information a user may process the CTP data again, for example, using a different or modified protocol via more or less user interaction.

In the illustrated embodiment, a plausibility checker 216 checks the data. In this instance, the data analyzer 122 can generate data indicating whether the CTP data should be processed again and/or recommend changes to the processing protocol and/or processing mode. In another instance, the output device 126 presents the output of the plausibility checker 216, and the user determines this information. In another embodiment, the plausibility checker 216 is omitted.

Figure 3:
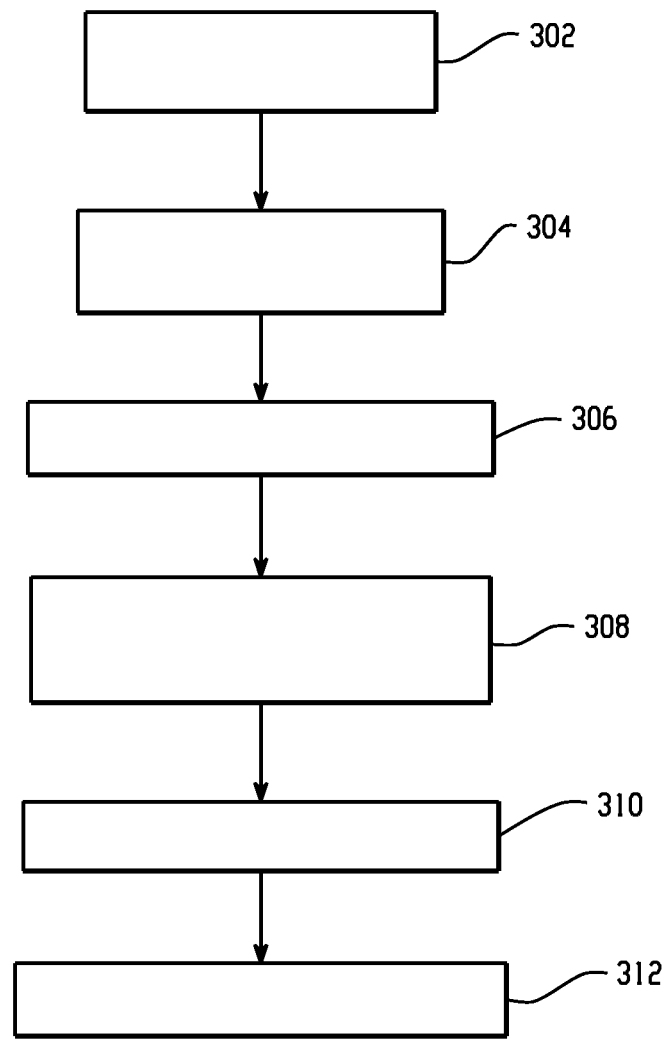
FIG. 3 illustrates an example method.

FIG. 3 illustrates a flow diagram.

At 302, a data set for processing is identified. As described above, suitable data includes imaging perfusion data generated by an imaging modality such as CT, MR, US, SPECT, PET, etc. data.

At 304, a processing protocol is identified. As described above, the identified protocol can be obtained from a protocol repository, derived therefrom, or newly generated. The protocol can be identified based on information such as imaging data, non-imaging data, and/or other information.

At 306, a processing mode is selected. The mode may be an automated, a semi-automated or a manual mode. The mode may be a default mode or a mode selected based on the imaging data, the non-imaging data, and/or the other information.

At 308, the data is processed, using the identified processing protocol, based on the selected mode. Such processing may also include various pre-processing such as registering image data, filtering image data, generating perfusion masks, segmenting the image data, identifying one or more reference vessels, generating one or more perfusion maps, generating a summary map and/or other processing.

At 310, a plausibility check is performed on the processed data, including one or more of the registered image data, the filtered data, the masks, the segmented data, the identified reference vessels, the one or more perfusion maps, and the summary map.

At 312, based on the plausibility check, the processing protocol may be changed or modified, and/or one or more of the processing steps may be performed using a different mode with a different degree of user interaction.

In another instance, the user may determine to perform one or more of the processing steps with user interaction before the data is processed at act 308. For example, if the user believes that the plausibility check is likely to fail, the user can change the mode of the data analyzer 122 to a semi-interactive mode.

The above may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
   executing, via a data analyzer, computer executable instructions that select, without user interaction, an imaging data processing protocol from an electronic repository of protocols based on imaging data corresponding to the patient;
   processing, via the data analyzer, reconstructed functional imaging data for a subject with the selected imaging data processing protocol under a first processing mode, wherein the selected imaging data processing protocol includes at least two processing steps;
   performing, automatically via a computer processor, a first plausibility check during execution of the selected imaging data processing protocol at least between the at least two processing steps; and
   changing, automatically via the computer processor, the processing mode from the first processing mode to a second processing mode based on the first plausibility check, wherein the data analyzer processes the functional imaging data under the second processing mode.

2. The method of claim 1, wherein the first and second processing modes respectively include different degrees of user interaction.

3. The method of claim 1, wherein the first mode processes the data without user interaction and the second processing mode processes the data with user interaction.

4. The method of claim 3, wherein the at least two processing steps includes:

registering image data from the patient data, producing registered image data, and performing the first plausibility check on the registered image data;

identifying reference vessels in the registered image data;

generating at least one perfusion map based on the registered image data and the identified reference vessels; and generating a summary map based on the at least one perfusion map.

5. The method of claim 4, further comprising:

performing a second plausibility check after execution of the selected processing protocol, wherein the second plausibility check includes evaluating the at least one perfusion map.

6. The method of claim 5, wherein the second plausibility check includes evaluating at least one of a shape of a time concentration curve or a location of the reference vessels or other feature(s) derived from the image data or the processed image data by the data analyzer.

7. The method of claim 4, further comprising:

performing a second plausibility check on the identified reference vessels in the registered image data; and changing the processing mode from the first processing mode to a second processing mode based on the second plausibility check, wherein the data analyzer processes the functional imaging data under the second processing mode.

8. The method of claim 3, wherein the at least two processing steps includes:

registering image data from the patient data, producing registered image data;

identifying reference vessels in the registered image data;

performing the first plausibility check on the identified reference vessels;

generating at least one perfusion map based on the registered image data and the identified reference vessels; and generating a summary map based on the at least one perfusion map.

9. The method of claim 1, wherein the processing protocol includes a plurality of computer executable acts, and the data analyzer performs at least one of the plurality of acts with user interaction if the first plausibility check is not satisfied, wherein the at least one of the plurality of acts was automatically performed prior to the first plausibility check.

10. The method of claim 1, further comprising changing the processing mode if a physiological state of the subject is not reflected in the selected processing protocol.

11. The method of claim 1, further comprising selecting a semi-interactive processing mode if it is determined that the selected protocol is likely to produce a result that does not satisfy the first plausibility check.

12. The method of claim 1, further including selecting the processing protocol based on non-imaging data corresponding to the patient, wherein the non-imaging data includes information indicative of one or more of a heart rate, a neurological symptom, a neurological deficit, or a vessel abnormality of the subject.

13. A data analyzer, comprising:

a computer processor that selects a processing protocol from a plurality of processing protocols stored in a protocol repository based on imaging data for a patient; employs the selected processing protocol to process patient data for the patient without user interaction, wherein the selected imaging data processing protocol includes at least two processing steps, wherein the computer processor, automatically, performs a first plausibility check during execution of the selected imaging data processing protocol at least between the at least two processing steps; and modifies, automatically via the computer processor, the selected processing protocol based on user input if the processed data fails to satisfy the first plausibility check, wherein the computer processor employs the modified processing protocol to process the patient data.

14. The data analyzer of claim 13, wherein the patient data includes computed tomography perfusion data.

15. The data analyzer of claim 13, the computer processor further transitions between an automated, a semi user interactive and a user interactive mode based on the first plausibility check.

16. The data analyzer of claim 15, wherein the mode transitions from the automated to one of the semi user interactive or the user interactive mode if the processed data fails to satisfy the first plausibility check.

17. The data analyzer of claim 13, wherein the selected processing protocol includes a plurality of computer executable acts, and the computer processor performs the plurality of acts without user interaction.

18. The data analyzer of claim 13, wherein the selected processing protocol includes a plurality of computer executable acts, and the computer processor performs at least one of the plurality of acts with user interaction if the processed data fails to satisfy the first plausibility check.

19. The data analyzer of claim 13, wherein the patient data includes perfusion image data, and the computer processor generates at least one perfusion map based on the patient data, wherein the computer processor performs a second plausibility check after execution of the selected processing protocol, wherein the second plausibility check includes evaluating the at least one perfusion map.

20. The data analyzer of claim 19, wherein the computer processor generates a summary map based on the at least one perfusion map.

21. A non-transitory computer readable storage medium containing instructions which, when executed by a computer, cause the computer to perform the steps of:

loading patient data, wherein the patient data includes input for post-processing to obtain diagnostic image data;

selecting a processing protocol from a database without user interaction and based on imaging data for the patient, wherein the selected imaging data processing protocol includes at least two processing steps;

processing the patient data with the selected processing protocol without user interaction;

performing a first plausibility check during execution of the selected imaging data processing protocol at least between the at least two processing steps; and if the processed data fails to satisfy the first plausibility check, modifying the selected processing protocol and processing the patient data with the modified processing protocol.

22. The non-transitory computer readable storage medium of claim 21, further containing instructions which, when executed by a computer, cause the computer to perform the step of: without user interaction, one or more of: registering image data for the patient data, performing the first plausibility check on the registered image data, identifying a reference artery in the image data, generating at least one perfusion map based on the registered image data and the identified artery or generating at least one summary map based on the perfusion map.

23. The non-transitory computer readable storage medium of claim 21, further containing instructions which, when executed by a computer, cause the computer to perform the step of: modifying the selected processing protocol based on one or more of a shape of a time concentration curve, a physiologic parameter of the patient, patient motion, information about contrast agent administration to the patient, a location of a reference vessel, a generated perfusion map, and CTP image data for the patient.

24. The non-transitory computer readable storage medium of claim 21, further containing instructions which, when executed by a computer, cause the computer to perform the following act: switching between interactive, semi-automatic and fully automatic processing modes.

* * * * *